United States Patent [19]
Verdonk et al.

[11] Patent Number: 5,485,845
[45] Date of Patent: Jan. 23, 1996

[54] ROTARY ENCODER FOR INTRAVASCULAR ULTRASOUND CATHETER

[75] Inventors: Edward Verdonk, Redwood City;
Michael Greenstein, Los Altos;
Hewlett E. Melton, Jr., Sunnyvale;
Mir S. Seyed-Bolorforosh, Palo Alto, all of Calif.

[73] Assignee: Hewlett Packard Company, Palo Alto, Calif.

[21] Appl. No.: 434,616

[22] Filed: May 4, 1995

[51] Int. Cl.$^6$ .................................................. A61B 8/12
[52] U.S. Cl. .................................................. 128/662.06
[58] Field of Search .................... 120/660.08, 660.09, 120/660.1, 662.03, 662.06, 662.05

[56] References Cited

U.S. PATENT DOCUMENTS

| | | | |
|---|---|---|---|
| 4,794,931 | 1/1989 | Yock | 128/660.03 |
| 4,917,097 | 4/1990 | Proudian et al. | 128/662.06 |
| 5,000,185 | 3/1991 | Yock | 128/662.03 |
| 5,054,492 | 10/1991 | Scribner et al. | 128/662.06 |
| 5,115,814 | 5/1992 | Griffith et al. | 128/662.06 |
| 5,131,397 | 7/1992 | Crowley | 128/662.06 |
| 5,176,141 | 1/1993 | Bom et al. | 128/662.06 |
| 5,186,177 | 2/1993 | O'Donnell et al. | 128/662.06 |
| 5,240,003 | 8/1993 | Lancee et al. | 128/662.06 |
| 5,243,988 | 9/1993 | Sieben et al. | 128/662.06 |
| 5,271,400 | 12/1993 | Dumoulin et al. | 128/653.2 |
| 5,271,402 | 12/1993 | Yeung et al. | 128/660.1 |
| 5,284,148 | 2/1994 | Dias et al. | 128/662.06 |
| 5,353,798 | 10/1994 | Sieben | 128/662.06 |

OTHER PUBLICATIONS ten Hoff, H. et al., "Imaging artifacts in mechanically driven ultrasound catheters," *International Journal of Cardiac Imaging*, 1989, pp. 195–199.
ten Hoff, H., "Scanning Mechanisms for Intravascular Ultrasound Imaging: a flexible approach," Erasmus University, Rotterdam, 1993 Thesis, pp. 117–151.

*Primary Examiner*—George Manuel

[57] ABSTRACT

An ultrasound system and method for intravascular ultrasonic imaging includes an array of beacons that are fixed to direct ultrasonic energy toward an imaging transducer, with individual beacons being identifiable in order to determine the angular position of the imaging transducer. Based upon the data related to beacon identification, operation of the imaging device is adaptively adjusted in order to compensate for variations in angular velocity of the transducer. Adaptive compensation may be performed by adjusting the pulse repetition rate of transmitted ultrasonic energy, by adjusting the scan conversion algorithm or mapping reflected ultrasonic energy, or by varying control of the drive structure for rotating the transducer. The beacons are preferably piezoelectrically active, but passive beacons may also be used. Position identification may be performed by techniques including amplitude sensing, phase sensing, pulse length sensing, and frequency sensing. As an alternative to rotation of the transducer, ultrasonic signals may be formed at a proximal end of a probe and then conducting the energy to the distal end via a waveguide.

22 Claims, 10 Drawing Sheets

ROTARY ENCODER FOR INTRAVASCULAR ULTRASOUND CATHETER

TECHNICAL FIELD

The invention relates generally to devices and methods for imaging the interior of a vessel, such as a blood vessel, and more particularly to devices and methods for reducing image distortion due to nonuniform rotational velocity of a rotating catheter.

BACKGROUND ART

Within the medical field, ultrasound systems are used for various imaging and treatment purposes. For example, there is an increasing appreciation of the diagnostic value of obtaining cross sectional images of coronary arteries by the method of intravascular ultrasound (IVUS). There are currently two general types of IVUS catheter systems. In a first type, subsets of an array of ultrasound transducers are sequentially excited in a manner to electronically steer an ultrasonic beam. This approach is sometimes referred to as the synthetic aperture focusing technique (SAFT). U.S. Pat. Nos. 4,917,097 to Proudian et al. and 5,186,177 to O'Donnell et al. describe use of this approach.

The second approach in the design of an IVUS catheter system is one in which the ultrasonic beam is redirected mechanically, rather than electrically. There are three subclasses of this mechanical approach. IVUS systems in the first subclass include either a rotating transducer or a rotating mirror in the distal end of the catheter that enters the vessel. A motor is coupled to the catheter at the proximal end that remains at the exterior of the bony. A drive shaft connects the proximal motor to the rotating distal transducer or mirror. U.S. Pat. Nos. 4,794,931 and 5,000,185 to Yock teach this technique. In the second subclass, rotation is confined to the distal end. U.S. Pat. Nos. 5,176,141 to Bom et al. and 5,240,003 to Lancee et al. teach incorporation of a micro motor at the distal end for rotating a transducer or a mirror. Alternatively, a fluid-driven turbine may be used to rotate the transducer or the mirror, as taught by U.S. Pat. No. 5,271,402 to Yeung et al., which is assigned to the assignee of the present invention. The third subclass is one in which the ultrasonic beam is generated at the proximal end of the catheter and is channeled to the distal end via a rotating waveguide, as taught by U.S. Pat. No. 5,284,148 to Dias et al., which is assigned to the assignee of the present invention.

The mechanical-rotating approach of directing an ultrasonic beam from a distal end of a catheter is more prevalently used than the approach of electronically aiming the beam. The mechanical approach can be implemented using a single transducer, while the electronic approach requires an array of transducers to be contained in the distal end that must pass through a vessel, such as a blood vessel. However, one concern in the use of an IVUS imaging system in which mechanical rotation is required is that the rotational velocity of the rotating structure will be nonuniform. A nonuniform rotational velocity will distort the image that is formed. One cause of nonuniformity with respect to the rotational velocity is the existence of mechanical friction and binding of the catheter as it spins in the tortuous path of the coronary arteries. Although the proximal end of the catheter is rotating at the desired velocity, any binding of the catheter along its length will lead to a distal rotational velocity that is different than the desired velocity. Assuming a constant proximal velocity from a drive motor variations in the distal velocity are typically related to storage of energy in the drive shaft in the form of torsion. If the catheter rotates at a velocity that is greater or less than the desired rotational velocity, reflected ultrasonic energy that is received from a particular location will be portrayed in the resulting image as being from an incorrect location.

Figure 1:
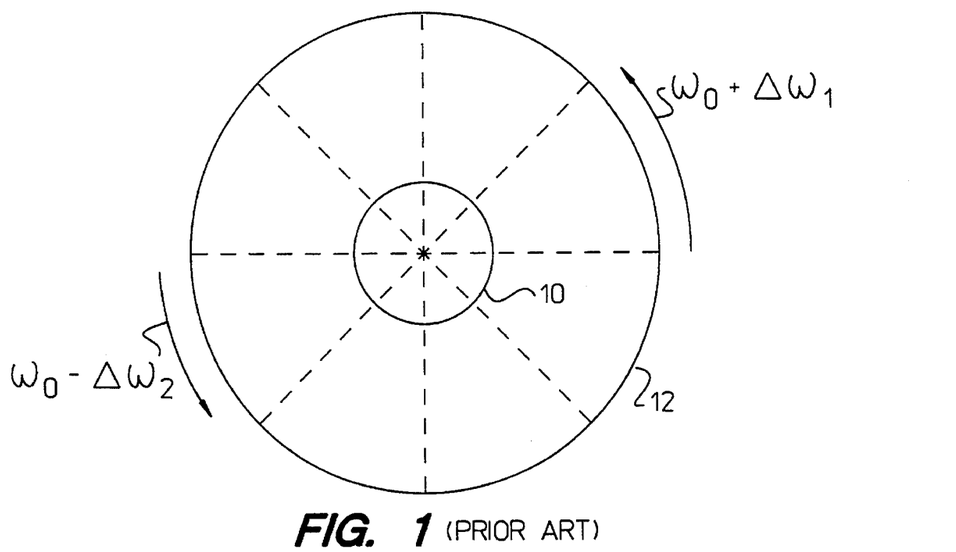
FIG. 1 is a sectional view of a catheter concentrically located within a vessel to be imaged, with the catheter having a biphasic velocity profile in accordance with the prior art.

With reference to FIG. 1, in the ideal, a catheter 10 is positioned coaxially with a vessel 12 for which ultrasonic intravascular images are to be formed. The catheter has a diameter that is relatively small compared to the diameter of the vessel. In this ideal situation, the catheter is rotated at a constant angular velocity, $\omega_0$. Thus, there is a one-to-one correspondence between the anticipated directions of ultrasound transmission and reception and the actual directions of transmission and reception. Electrical signals generated in response to a reception of reflected energy may be accurately collected, processed and displayed.

Figure 2:
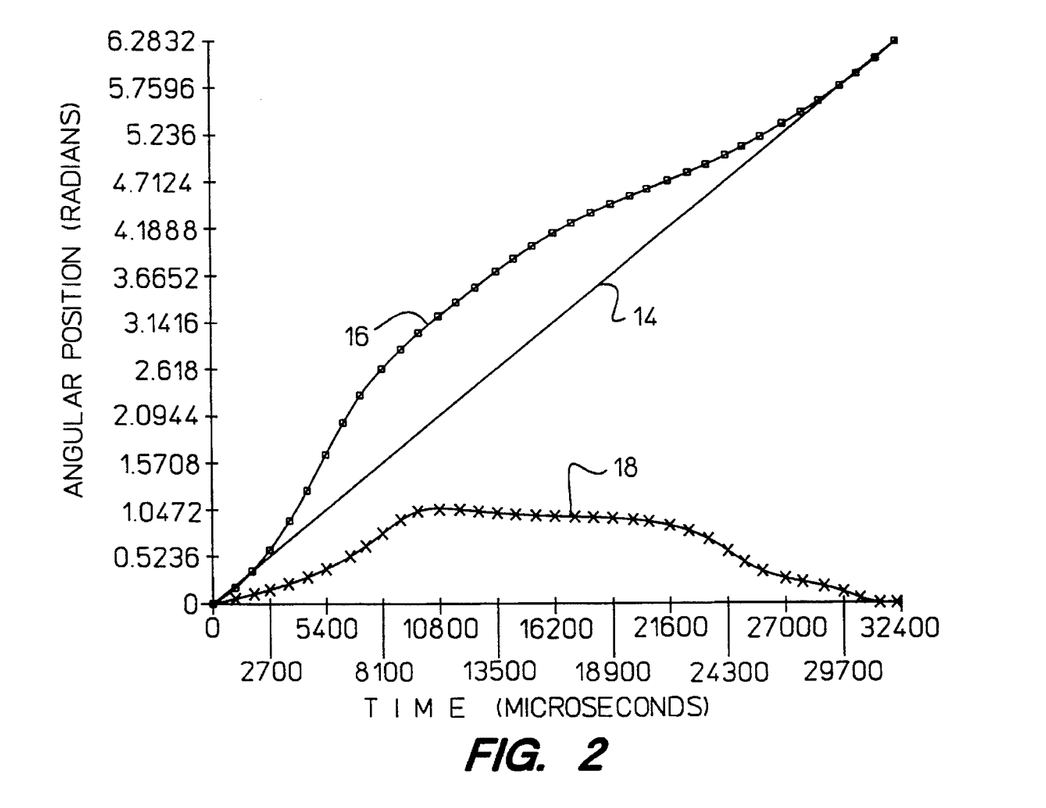
FIG. 2 is a plot of an angular error curve as a difference between anticipated and actual angular position.

Rather than a constant rotational velocity, FIG. 1 illustrates a "biphasic velocity profile," in which the catheter is rotating too quickly, $\omega_0 + \Delta\omega_1$, for a portion of each revolution and too slowly, $\omega_0 - \Delta\omega_2$, for another portion. By integrating the rotational velocity as a function of time, it is possible to obtain the angular position as a function of time. In FIG. 2, the anticipated rotational velocity is a constant, thereby producing a straight line 14 having a slope of $\omega_0$. However, the actual biphasic velocity profile with an excessive rotational velocity over a first portion of each cycle and a diminished rotational velocity over a second portion is shown by plot 16. The difference between the anticipated rotational velocity 14 and the actual rotational velocity 16 is shown at plot 18, which is referred to as the angular error curve (AEC). The AEC determines the degree of error of an image.

Figure 3:
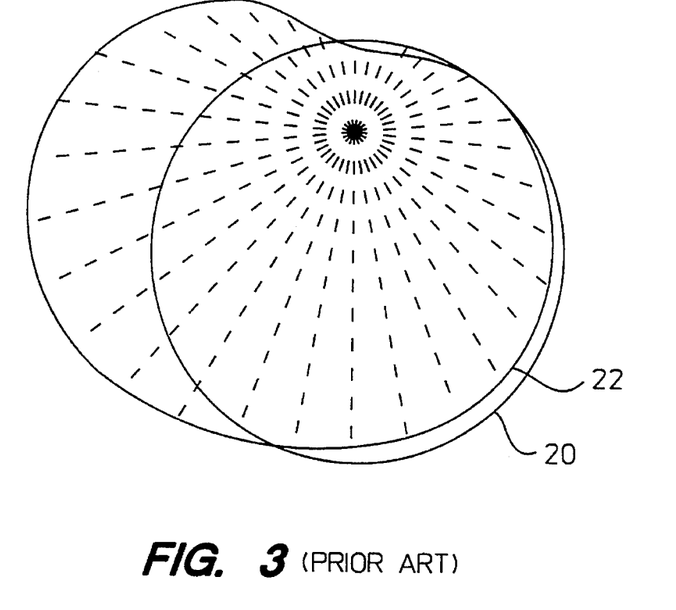
FIG. 3 is an illustration of shape distortion due to a biphasic velocity profile and eccentric placement of a catheter in accordance with the prior art.

The combination of nonuniform rotational velocity and eccentric catheter placement can lead to the distortion of the shape of a vessel wall. As an example, FIG. 3 shows an actual vessel wall 20 compared to the image of the actual vessel wall when a catheter has a biphasic velocity profile and is located eccentrically as illustrated. The dotted lines in FIG. 3 represent the ultrasound A lines, which are fired either too early or too late as a result of the incorrect velocity. For each ultrasound A line which is too early or too late, the angular position information to imaging equipment is incorrect. On the other hand, the range information to the imaging equipment is correct. Thus, the correct range information is rotated by the imaging equipment to the anticipated angular orientation in order to calculate the portrayal of the vessel wall range segment. The distorted image of the vessel wall is then constructed as the spline which connects all the "rotated" A lines. FIG. 3 illustrates an overestimation of the vessel area, as well as a distortion of the local curvature of the wall. Underestimations of the lumen area are also possible with different eccentric placements of the catheter.

Previous attempts to measure the position, or orientation, of the transducer have included a fluoroscope marker, as taught by Scribner et al. in U.S. Pat. No. 5,054,492, a magnetic resonance imaging-based tracking system, as taught by Dumoulin et al. in U.S. Pat. No. 5,271,400 and an external ultrasound-based system, as taught by Crowley in U.S. Pat. No. 5,131,397. While each of these systems operates sufficiently for its intended purpose, each system requires bulky and expensive additional equipment in order to perform the IVUS imaging of a vessel wall. Moreover, none of the systems recognizes the nonuniform rotational velocity problem or addresses a solution to the problem.

U.S. Pat. No. 5,243,988 to Sieben et al. describes the use of markers, preferably periodic variations in wall thickness of the catheter sheath, as a means for rotary encoding, but concerns exist. First, the numbers identified in the patent with regard to the sheath thickness and the transducer frequency are such that the walls are likely to be too thin to be resolved. Second, the abrupt changes in wall thickness may cause distortion of the ultrasound beam, due to refraction, unless the speed of sound in the sheath is close to that in water, which is not true for most plastics that are used to construct conventional sheaths. The distortion of the beam would result in degradation of image quality. Moreover, abrupt changes in wall thickness reduce the number of angular positions that can be encoded.

In a thesis entitled "Scanning Mechanisms for Intravascular Ultrasound Imaging: A Flexible Approach," Erasmus University, Rotterdam, 1993, by H. ten Hoff, non-uniformity of angular velocity was again addressed. Acoustic, capacitive, electromagnetic and optical techniques were considered as means for angle detection. Correction of the image was then performed in one of two ways. According to one method, an angle detection signal was used to measure or estimate the traversed angle between two successive directions of ultrasonic transmission, emitted at equal time intervals. The resulting information was then fed to display processing for correctly positioning the corresponding image-lines. H. ten Hoff concluded, however, that the tangential resolution became dependent upon the rotational angle, which diminished the image quality. The second method was one of using the angle detection signal to trigger the emission of ultrasonic pulses at equal traversed angle increments, so that image-lines were then generated periodically. The paper briefly referred to use of acoustic techniques to determine the angle detection signal, but focused upon optical determination because of a number of identified drawbacks to the acoustic solution. The identified drawbacks included low resolution of ultrasonic reflecting structures, multiple reflection, and shadowing.

What is needed is an ultrasound device and method by which the angular orientation of a catheter tip can be tracked in real time in order to reliably and repeatedly identify the position and properties of a specific anatomic structure, such as calcified plaque, and to adaptively correct angular velocity profiles which potentially extend over more than one rotational cycle.

SUMMARY OF THE INVENTION

The above object has been met by an ultrasound device and method that utilize beacons that are positioned to either reflect (passive) or transmit (active) ultrasonic energy toward a rotating transducer. Typically, the beacons are in a field of view of the rotating ultrasound transducer used to image anatomic structures. The beacons should be configured and positioned to minimize their effect upon an image to be formed. Moreover, since the beacon positions are known, it is possible to boost the gain of those segments of rf A-lines corresponding to signals from structures lying beyond the beacon positions, with the boosting of the gain being relative to those segments of the rf A-lines corresponding to signals from the beacons. Gain can be adjusted to compensate for reduced signal strength due to partial reflection of sound from the beacons. In practice, beacons may be placed at the exterior or the interior of a sheath that houses the transducer. Each beacon preferably has a unique "acoustic signature," thereby allowing each beacon to be uniquely identified. This may be achieved by tailoring the acoustic properties of each beacon (e.g., the acoustic impedance of a passive beacon) and/or by varying with angular position the ultrasound signal used to interrogate the beacons.

With regard to the operation of the beacons, three basic steps are involved in overcoming image distortions due to nonuniform rotational velocity. The three steps are: directing energy from the beacon; identifying individual beacons; and providing adjustments in response to detection of a variation in angular velocity.

Passive beacons, i.e., beacons that redirect rather than transmit acoustic energy, are the preferred embodiment, since the use of passive beacons requires the least amount of modification to existing IVUS imaging systems. As one alternative, the passive beacons may be formed of a material that provides a change in acoustic impedance. In an active-beacon embodiment, the beacons may be a layer of piezoelectric material between two electrode layers. When an electrical signal is formed across the electrode layers, the piezoelectric layer transmits an ultrasonic signal to the rotating transducer, which then converts the ultrasonic signal back to an electrical signal for identification of the individual beacon by external imaging equipment.

The second step involves individually identifying beacons in order to permit calculation of angular velocities of the rotating transducer. The second and third steps may be performed during a normal imaging sequence or during a pre-image calibration sequence. As previously noted, there are two approaches to uniquely identifying the beacons. These approaches may be used alone or in concert. In the first approach, the beacons themselves are physically different and are interrogated with identical ultrasonic signals. For example, by varying the reflection coefficient of the beacons, it is possible to encode angular position as a function of the amplitude of the reflected signal. In the second approach, the beacons are physically identical, but are distinguished from one another by varying the ultrasonic signal that they reflect (passive) or broadcast (active). One example of this second approach involves passive beacons and a variation in the number of cycles per burst (pulse length) transmitted by the rotating transducer, with the variation being a function of the anticipated angular position. By counting the number of cycles in the signal reflected from each beacon, the actual angular position can be determined and compared to the anticipated angular position in order to detect errors in the angular velocity. Angular velocity errors encompassing more than one revolution can be detected by monitoring the number of cycles returned from each beacon over a number of revolutions. Alternate embodiments are contemplated, wherein other characteristics of the ultrasonic signal are used to encode angular position, such as the use of the characteristics of amplitude, phase and frequency. The two approaches apply equally to utilization of passive beacons and active beacons.

As yet another alternative to actually varying the characteristics of ultrasonic signals propagating between the beacons and the imaging transducer, identical ultrasonic signals may be received at the rotating transducer, but then the signals may be processed in a manner to determine beacon identity. As an example of this alternative, the ultrasonic signals received at the transducer from the beacons are converted into electrical signals and referenced to an internal electrical signal having a characteristic that varies with the anticipated angular position of the transducer. The reference signal may increase or decrease in frequency for a multiple of the anticipated period of a transducer revolution. By mixing the reference and beacon signals, the mixed signal may be monitored to detect differences between the actual mixed frequency and the frequency that is anticipated when the transducer is rotated at the constant selected angular velocity.

Velocity error can then be determined using the acquired data from the operation of identifying individual beacons. For example, an angular error curve 18 of FIG. 2 may be calculated by comparing the anticipated angular position with the actual angular position as a function of time.

The third operation identified above is the correction of a calculated error. In a first embodiment of adaptive adjustment, the repetition rate of ultrasound pulses from the rotating transducer is varied to achieve uniform angular increments between adjacent radio frequency A lines, regardless of rotational velocity. That is, the variations in rotational velocity remain uncorrected, but the pulse repetition rate varies to provide compensation. In a second embodiment, the scan conversion algorithm of external imaging equipment is affected such that while the angular sampling by the transducer may be nonuniform, the imaging equipment recognizes the nonuniformity and provides compensation at the imaging level. In the third embodiment, the rotational drive structure is controlled for the purpose of reducing the nonuniformity. For example, current to a drive motor may be increased when the transducer has a tendency to slow down and the current may be decreased when the transducer has a tendency of speeding up.

An advantage of the invention is that the angular orientation of the transducer can be tracked throughout rotation without a significant increase in the cost of intravascular ultrasound imaging equipment. A more reliable cross sectional image of a blood vessel is thus achieved.

BEST MODE FOR CARRYING OUT THE INVENTION

Figure 4:
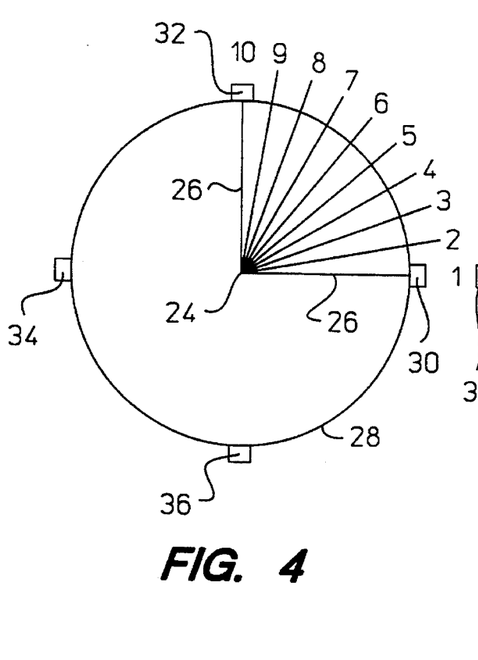
FIG. 4 is an operational view of the ideal for operating a catheter having beacons in accordance with the invention.

With reference to FIG. 4, in the ideal, ultrasonic energy is directed from a center 24 of a catheter for radiation in a rotary pattern. Ten lines 26, numbered 1–10, are shown in FIG. 4 as being equally spaced over a 90° sector of the catheter. All lines pass outwardly beyond a sheath 28 that houses the ultrasound transducer for generating the lines in response to an electrical signal.

Line 1 contacts a first beacon 30. Line 10 is directed at a second beacon 32. A third beacon 34 and a fourth beacon 36 are also shown in FIG. 4.

The earliest arriving signals for lines 26 are representative of energy partially reflected back to the center 24 of the catheter. Reflected ultrasonic energy from the beacons is converted to an electrical signal by the transducer and is used to calibrate the rotational velocity. Later arriving signals on these lines, and all others, represent scattering from structures beyond the catheter and are used to form an image. As will be explained more fully below, a device and method are required to monitor early time segments of each line to detect whether or not a line is bearing on one of the plurality of beacons. This information can then be used to calibrate the rotational velocity of the catheter tip.

Typically, the number of lines 26 within a 90° sector greatly exceeds the number illustrated in FIG. 4. Likewise, there are preferably more than four beacons 30–36. The reduced numbers of lines and beacons are selected for the purpose of illustration.

Figure 5:
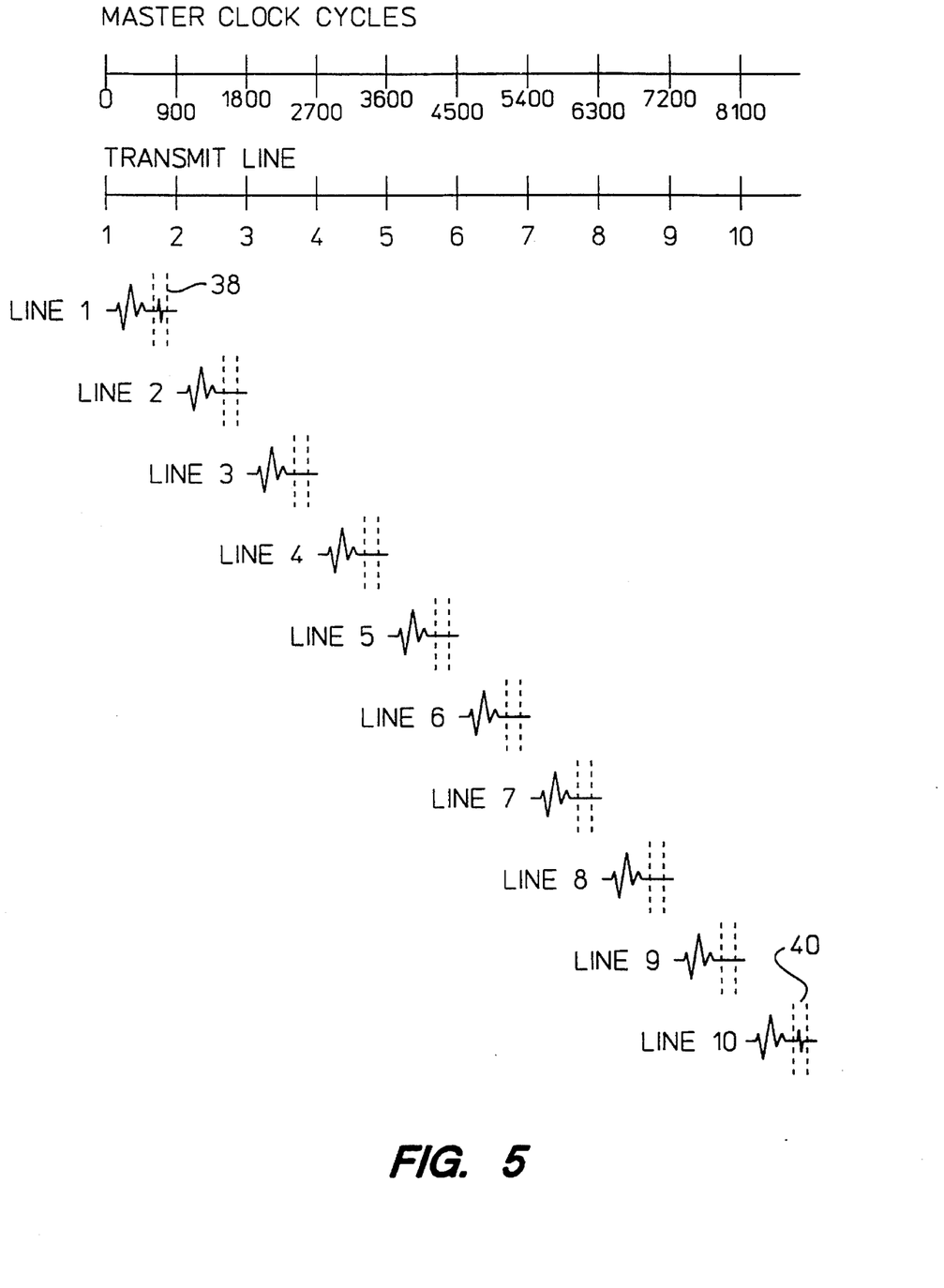
FIG. 5 is an illustration of a plurality of transmitted rf A-lines demonstrating reflected energy on those lines bearing on a beacon. Such reflections arrive earlier than backscattered energy from the tissues being imaged, since these tissues lie distal to the beacons.

In the imaging of a vessel, a frame of data may be collected in 32,400 μsec. That is, a rotary pattern of ultrasound transmission is completed within this time period. This yields a frame rate of approximately 31 frames/sec. In FIGS. 4 and 5, each frame includes 36 RF A-lines, so that reflected A-lines occur every ten degrees. In the ideal uniform rotational velocity of FIG. 4, this requires that the transducer be fired every 900 μsec. Assuming a master clock running at 1 MHz, the transducer is fired every 900th cycle of the master clock. Upon completion of a 90° rotation, line 10 is fired and data collection begins for the second 90° sector.

Data collection for the ten A-lines is shown in FIG. 5. Since the transducer-beacon separation is fixed and is known, it can be expected that for those A-lines in which the transducer is bearing on a beacon, a reflected echo will be received at the transducer at a predetermined time, with the number of these fixed-time beacon echoes that are received within each frame being equal to the number of beacons. Thus, a "watch" period early in each A-line can be established, during which the system "looks" for an echo from a beacon. For example, in FIG. 5 the watch periods are shown within dashed lines, and watch periods 38 and 40 of lines 1 and 10, respectively, are shown as including echoes reflected from the first and second beacons 30 and 32 back to the transducer. Because the echoes from beacons 30 and 32 were received on those A-lines for which echoes are to be anticipated when the rotational velocity is fixed at the desired rotational velocity, velocity correction is not required.

The reflected energy of A-line 1 during the watch period 38 identifies the angular position of the transmitter, since the position of the beacon is fixed and known. In the same manner, the angular position of the transducer during reception of the A-lines 10 is identifiable, since the beacon-reflected ultrasonic energy is received during watch period 40.

Figure 6:
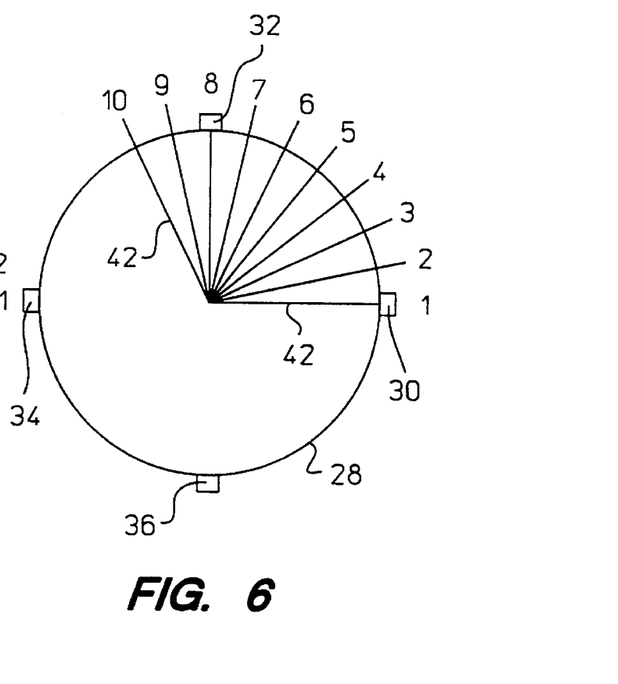
FIG. 6 is an operational view of a catheter in which a transducer is rotating at an excessive angular velocity.

Referring now to FIG. 6, ten A-lines 42 are transmitted and received during the same time sequence described above, but with the catheter rotating at an excessive speed. That is, the pulse repetition rate (PRR) is the same as that of FIG. 4, but the actual rotational velocity is greater than the anticipated rotational velocity. As a result, there is an angular under-sampling of the 90° sector defined by the first and second beacons 30 and 32. The A-line 8 is extended along the radius intersecting the second beacon 32, while A-lines 9 and 10 extend into the second 90° sector of the rotational pattern. On the other hand, the scan conversion algorithm of the external imaging equipment continues to map the ten A-lines through a 90° sector, rather than the actual 115.7° that the catheter has rotated during 8100 μsec.

Figure 7:
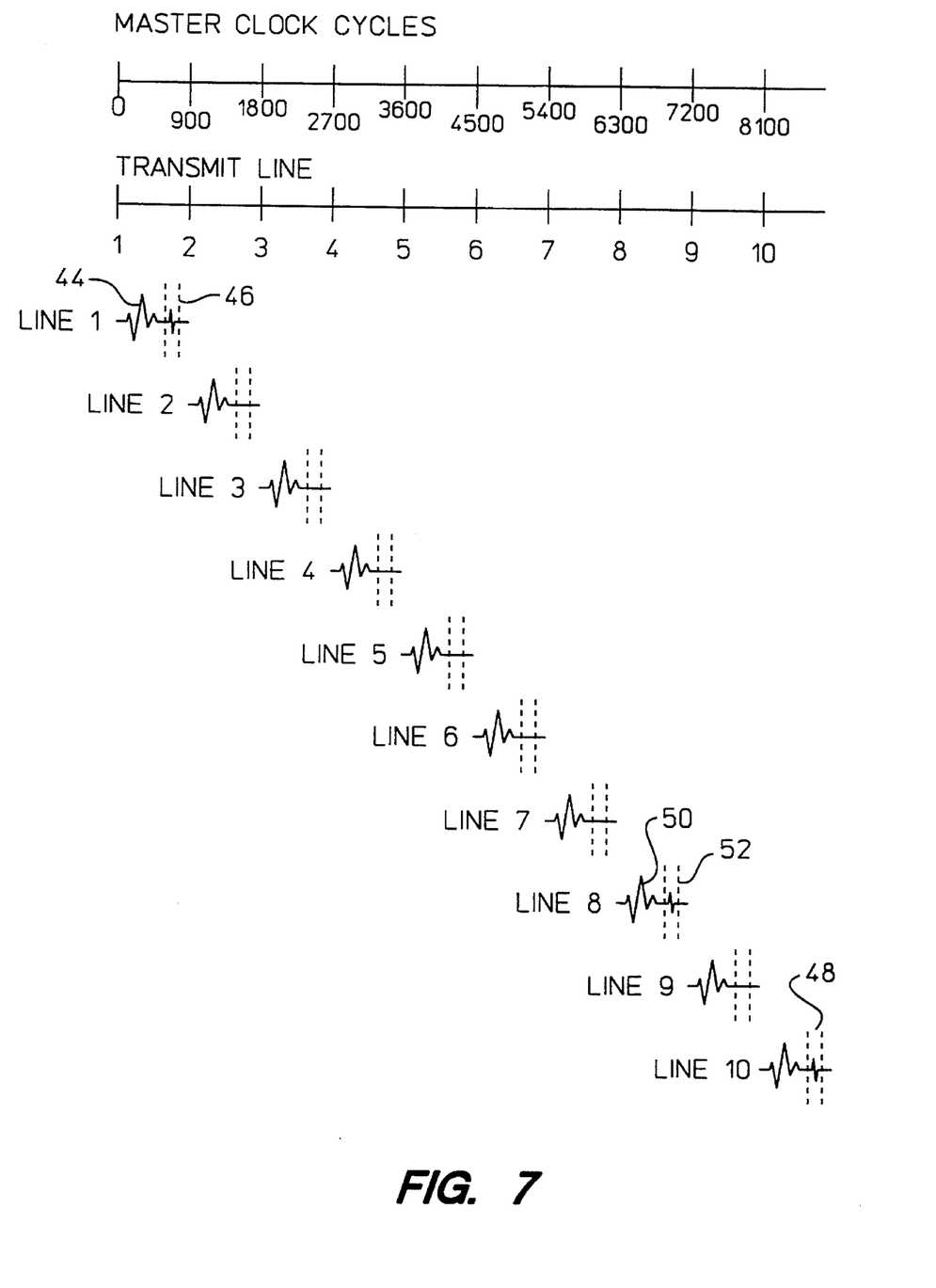
FIG. 7 is a view of the energy reflected from the beacons back to the transducer in response to the ten pulses of FIG. 6.

The ten A-lines of FIG. 6 are represented in FIG. 7. The A-lines 1 includes transmitted energy 44 and reflected energy during a watch period 46. The watch period is defined by the known time required to receive reflected energy from a beacon that is spaced from a source by a fixed distance. With the catheter rotating at a speed greater than the anticipated speed, the watch period 48 of A-lines 10 does not include reflected energy from a beacon. Instead, transmitted energy 50 of A-lines 8 is reflected and received during a watch period 52. As will be explained more fully below, compensation for the difference between actual and anticipated rotational velocity is designed to reduce imaging distortions that would otherwise result.

The rotational velocity represented by FIGS. 6 and 7 is excessive by a factor of 115.7°/90°, i.e. approximately 1.2856. One form of compensation would be to increase the PRR by the same factor. That is, the time between transmission of adjacent A-lines 42 must be decreased by the reciprocal of 1.2856. If n is the number of clock cycles between bursts, i.e. pulses, for the "corrected" PRR, then 90/115.7=n/900, so that n is equal to approximately 700. By decreasing the number of clock cycles between transmit pulses, it is possible to once again collect nine equally-spaced RF lines in a 90° sector, despite the fact that the catheter is rotating at a faster rotational velocity than anticipated by the external imaging equipment. In another embodiment, the PRR remains uncorrected, and it is the scan conversion algorithm of the external imaging equipment that is affected in order to compensate for the difference between anticipated and actual rotational velocity. Changing the scan conversion algorithm in response to detected variations in angular velocity would be within the skill of a person within the art. However, the concern with this compensation approach is that resolution of imaged anatomical structures may be adversely affected in some cases. A third approach of providing compensation involves adaptively controlling mechanical drive of the catheter. For example, the electrical current to a rotational drive motor may be varied in response to detected velocity variations. While this approach will significantly reduce distortions, there are concerns that compensation will be hindered by the inertial effect of the catheter and other driven structure.

Figure 8:
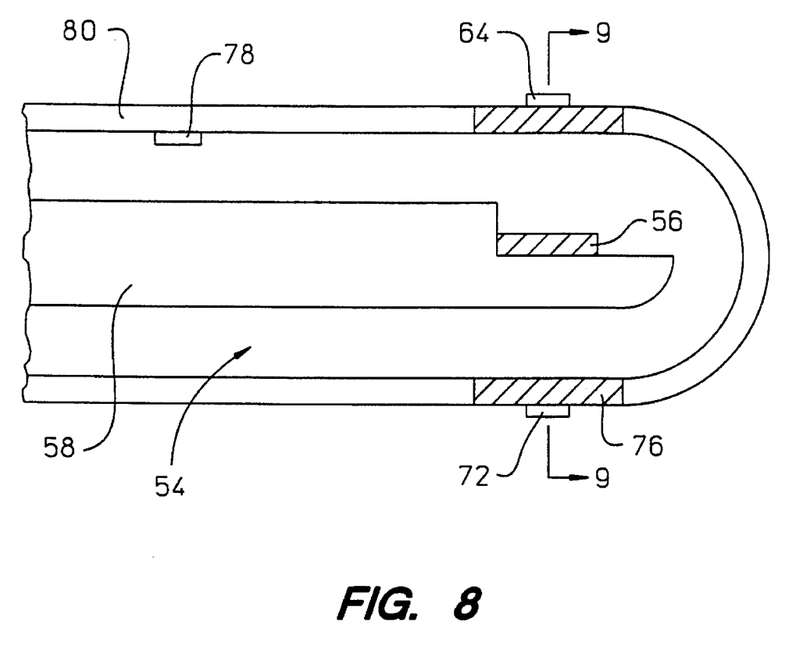
FIG. 8 is a side sectional view of a catheter having beacons positioned in accordance with the invention.
Figure 9:
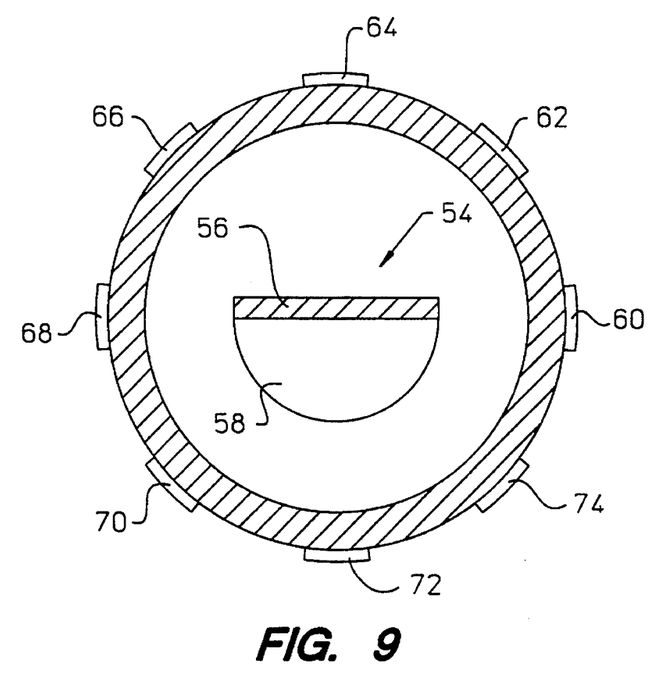
FIG. 9 is a cross sectional view of the catheter of FIG. 8 taken along lines 9—9.

Referring now to FIGS. 8 and 9, a catheter 54 is shown as having a transducer 56 mounted to a rotor 58. The transducer-and-rotor arrangement may be of any type known in the art. For example, the transducer 56 may be a piezoelectric layer sandwiched between electrode layers for conversion between electrical energy and ultrasonic energy.

On the exterior of the catheter 54 is an array of eight passive beacons 60, 62, 64, 66, 68, 70, 72 and 74. The only strict requirement of a beacon is that its position relative to the catheter be known. The externally mounted beacons are in the field of view of the ultrasound transducer 56. The beacons are mounted on an acoustic window 76 through which ultrasonic energy is transmitted and received.

In the passive mode, the beacons 60–74 act as reflectors for ultrasound being transmitted by the catheter 54. It is important that the passive beacons be sufficiently reflective to appear as "bright spots" on an image, but not so bright that the spots shadow points in the field behind them. The passive beacons provide zones of varying acoustic impedance, so as to yield corresponding changes in reflectivity. Passive beacons may be formed of evaporated, sputtered or electroplated metal film, but this is not critical. Alternatively, an integrated impedance matching layer can be formed at the surface of the sheath. This might, for example, involve forming microgrooves in the sheath material and backfilling these microgrooves with a material that has a different acoustic impedance. The acoustic impedance and/or velocity of sound through this integrated impedance matching layer can be varied spatially by spatially varying the volume fraction of microgrooves in the sheath.

The beacons 60–74 permit identification of the angular position of the catheter 54, but should not introduce artifacts that adversely affect imaging of anatomical structures. In software, the gain profiles of the A-lines that must "pass through" a beacon can be adjusted, so that shadowing of tissue behind the beacon can be overcome. Another alternative is to form the beacons to be acoustically transparent at the imaging frequency, but reflective at some other frequency. For example, a thin metal film may have a thickness that is a substantial fraction of a wavelength at a high frequency, but substantially acoustically transparent at a lower frequency. The catheter 54 may have two different transducers at the distal end. However, this technique is more easily implemented in use with an acoustic waveguide, wherein ultrasonic energy is generated at the proximal end and channeled to the distal end using waveguide principles. An intravascular imaging device having an acoustic waveguide is described in U.S. Pat. No. 5,284,148 to Dias et al., which is assigned to the assignee of the present invention. The acoustic waveguide works equally well with multiple frequencies.

Another approach for minimizing artifacts produced by the beacons 60–74 is to use a single transducer which is rotated at one angle during imaging and at a second angle during calculation of angular velocity. At the imaging angle, the beacons are outside of the field of view of the single transducer. Alternatively, the single transducer may be repositioned during determination of angular velocity. In FIG. 8, a beacon 78 is shown as being mounted on the interior of the sheath wall 80. The rotor 58 and transducer 56 may be aligned with the beacon 78 during calculation of an angular error curve, and then aligned with the acoustic window 76 during an imaging procedure. In this embodiment, beacon 78 is one of an array of beacons and the beacons 64–74 are omitted.

Figure 10:
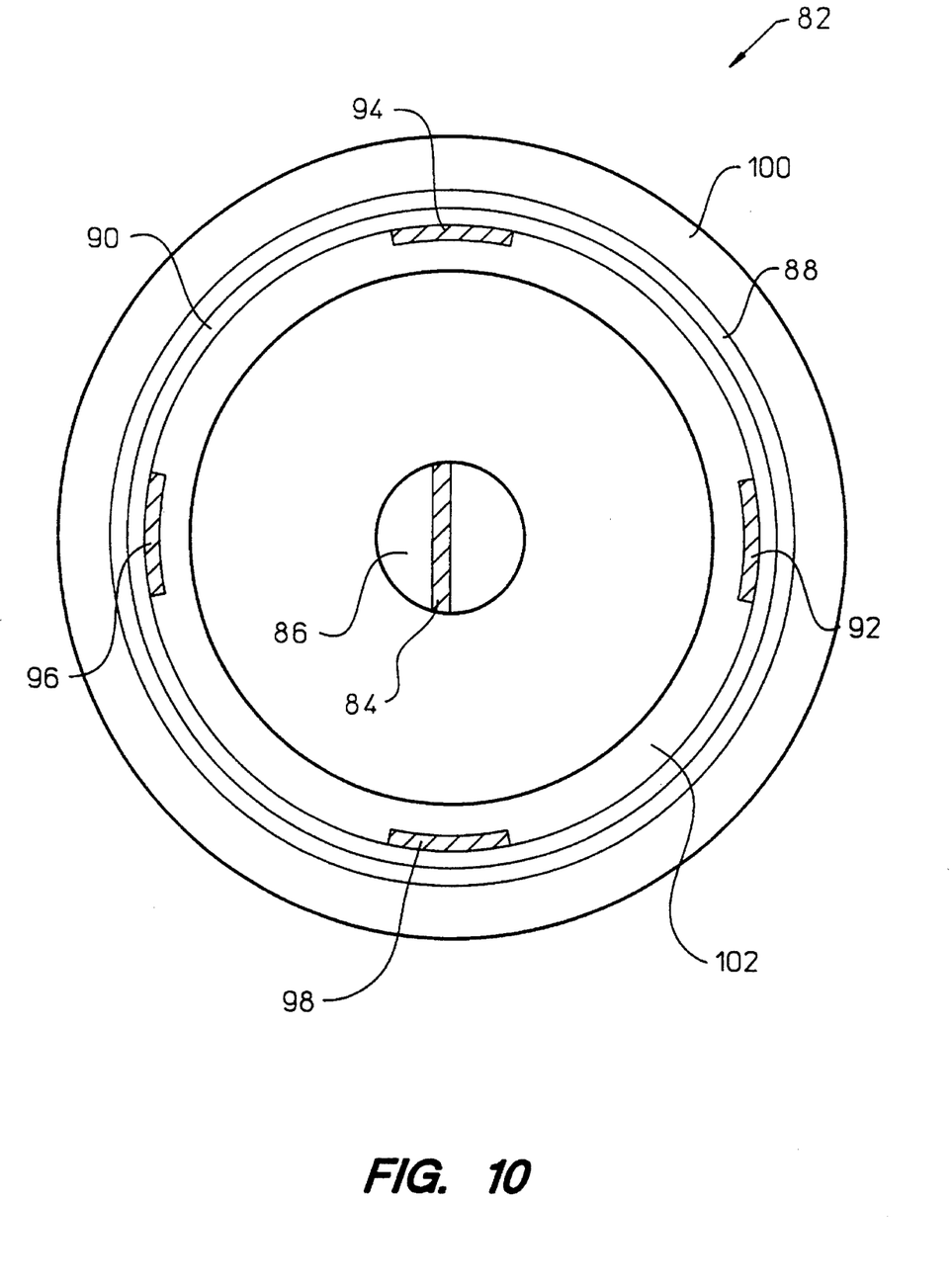
FIG. 10 is a cross sectional view of a catheter having piezoelectrically active beacons in accordance with the invention.

Referring now to FIG. 10, in an alternate embodiment, the distal end 82 of the device includes piezoelectrically active transducers. Thus, small transducers in the sheath wall generate ultrasonic energy in the direction of the rotating transducer 84. The rotating transducer is mounted on a drive shaft 86. The beacons include a continuous outer ground electrode 88 and a continuous piezoelectric layer 90. The positions of the active beacons are defined by a pattern of inner electrodes 92, 94, 96 and 98. When an electrical signal is connected across ground electrode 88 and the patterned electrodes 92–98, the areas of the piezoelectric layer 90 between the patterned electrodes and the ground electrode generate acoustic energy corresponding to the applied signal. In operation, the active beacons may be continuously transmitting as the imaging transducer 84 rotates. The imaging transducer receives the signals from the four active beacons, and the external imaging equipment identifies the individual beacons in order to determine the angular position of the imaging transducer. Typically, the device includes more than four active beacons.

The signals of the active beacons may be identical, with the external imaging equipment being operated to distinguish the beacons using one of the methods described below. Alternatively, the characteristics of beacon signals may be varied, such that the source of a beacon signal may be identified by analysis of the signal. For example, the amplitudes of the electrical signals to the patterned electrodes 92–98 may increase from electrode to electrode. As a result, the amplitudes of the generated beacon signals will increase correspondingly. Alternatively, the beacons may vary with respect to transmission frequency. However, this typically requires that the piezoelectric material vary in thickness from beacon to beacon, since the resonant frequency of a piezoelectric layer changes with the thickness of the layer. Another signal characteristic that can be varied is phase. Delays in the application of an excitation signal from one electrode 92–98 to the next electrode may be used as a method of providing phase-shifted, beacon-identifying signals.

The outer covering 100 of the distal end 82 may be formed of nylon, while an inner shell 102 may be formed of polyethylene. The patterned electrodes 92, 94, 96 and 98 may be formed of gold on the surface of the piezoelectric layer 90. The continuous ground electrode 88 may also be gold. A PVDF copolymer may be used as the piezoelectric layer 90. However, none of these materials is critical to the invention.

Using techniques known in the art, the regions of the continuous piezoelectric layer 90 associated with the patterned electrodes 92–98 are made active by poling, while regions adjacent to the patterned electrodes remain piezoelectrically passive. Wiring to the electrodes may extend from the proximal end of the device, but it is possible to house a signal generator within the distal end 82 for excitation of the active beacons.

In another embodiment, the active beacons associated with the patterned electrodes 92–98 are used as receptors, rather than transmitters. In this embodiment, the angular position of the imaging transducer 84 is determined by monitoring which active beacon is receiving acoustic energy from the imaging transducer.

Figure 11:
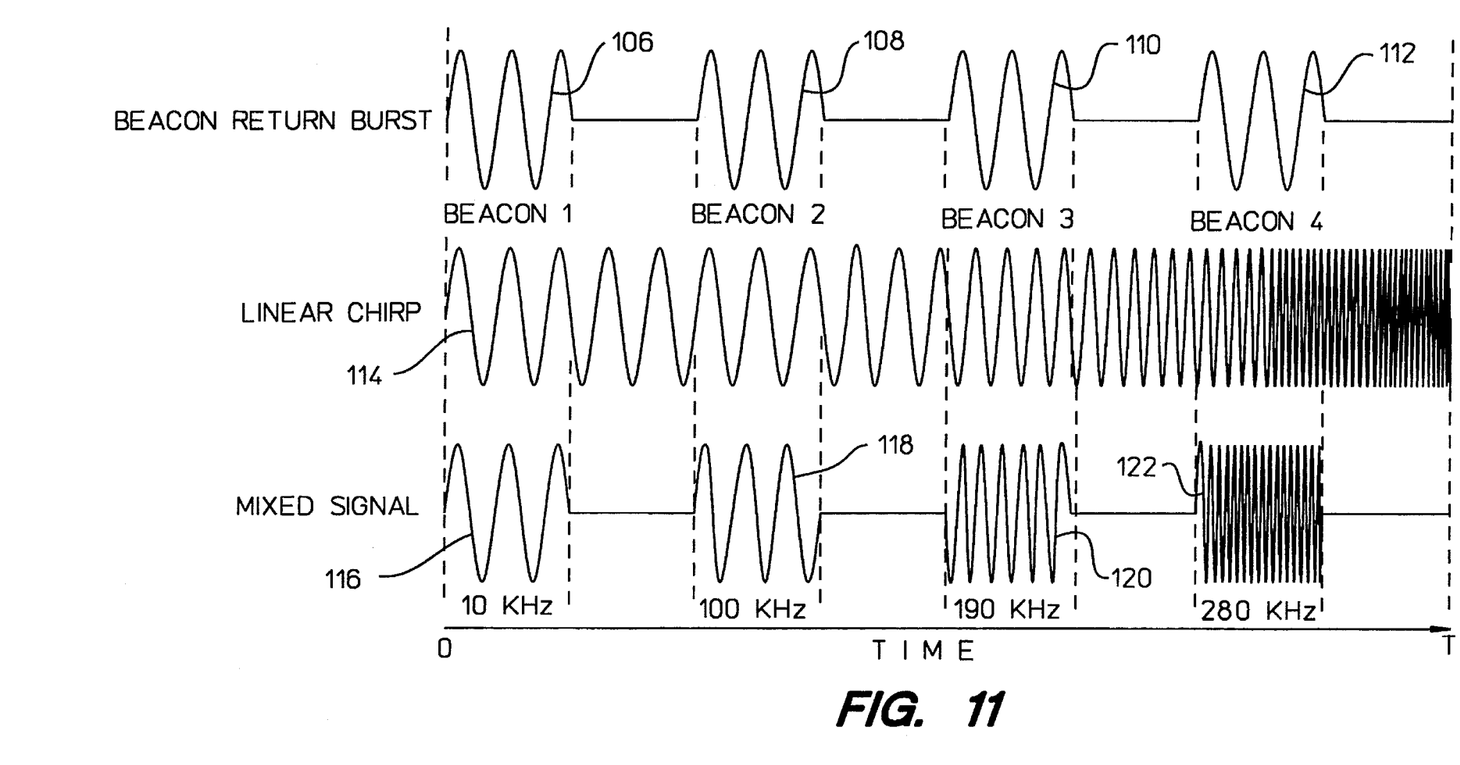
FIG. 11 is a plurality of waveforms for identifying individual beacons in accordance with one embodiment of the invention, with a transducer being rotated in the ideal.

Referring now to FIGS. 4 and 11, identification of individual beacons 30, 32, 34 and 36 may be accomplished by a frequency detection method. An ultrasonic signal is transmitted from the center 24 of the catheter. A beacon return burst 106, 108, 110 and 112 is directed toward the center 24 from each of the four passive beacons. The return bursts are received by an imaging transducer in sequence as the imaging transducer is rotated. A reference signal 114, referred to herein as a "chirped" signal, is mixed with the return bursts. The reference signal sweeps in frequency from a starting frequency to a peak frequency in the time of one period of nominal rotation, i.e. the anticipated time for completing one transducer rotation. The mixing of the return bursts with the reference signal 114 is carried out to provide four mixed signals 116, 118, 120 and 122. The mixed signals increase in frequency. A graph of the change in frequency to the change in angular position of the imaging transducer will yield a straight line when the rotational velocity of the transducer is constant.

Figure 12:
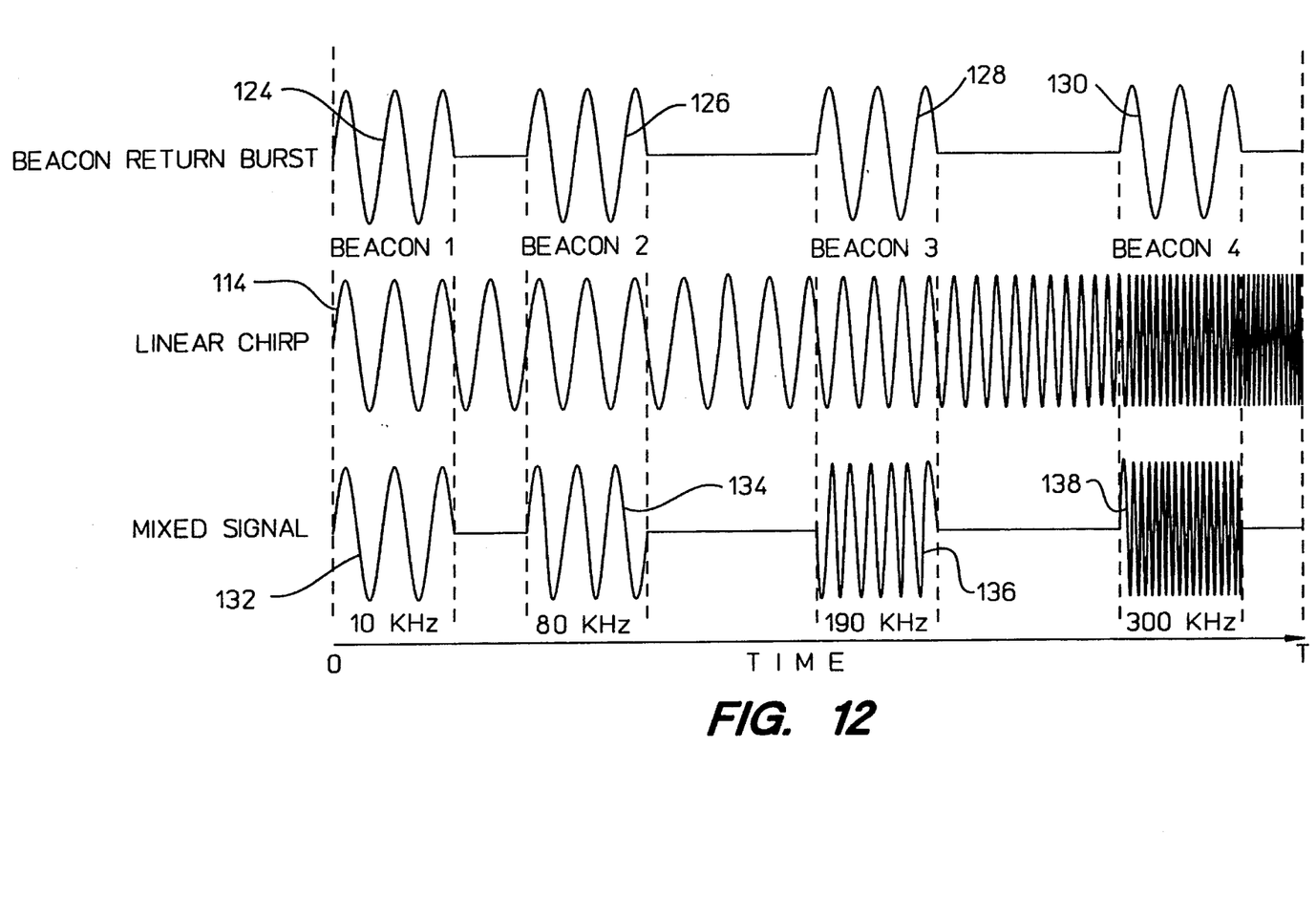
FIG. 12 is a plurality of waveforms corresponding to those of FIG. 11, but with the transducer having a nonuniform rotational velocity.

If the imaging transducer has an actual rotational velocity that exceeds the anticipated rotational velocity between the first beacon 30 and the second beacon 32, as represented in FIG. 6, and if the actual rotational velocity is below the anticipated velocity with travel from the second beacon to the fourth beacon 36, operation will be as shown in FIG. 12. The return bursts 124, 126, 128 and 130 are identical to those of FIG. 11, other than with regard to timing. The excessive speed causes the return bursts 126 from the second beacon 32 to be too closely spaced to the first return burst 124. In comparison, the time between other return bursts is excessive. The reference signal 114 increases in frequency in the same manner described above. The mixed signals 132, 134, 136 and 138 formed by referencing the four return bursts with the chirped signal are not proportional with regard to increases in frequency. Consequently, a plot of frequency change to angular position of the imaging transducer will not be a straight line. The difference between the actual plot and the anticipated straight-line plot is an angular error curve (AEC) that can be employed to provide compensation using one of the approaches described above, i.e. PRR adjustment, A-lines mapping adjustment, or drive adjustment. Other compensation techniques may also be utilized.

The "interrogation" of return bursts 106–112 and 124–130 by means of a reference signal 114 in order to individually identify beacons has been described with regard to correcting errors encountered over a single revolution of the catheter. However, the technique may be adapted to detect variations in angular velocity that are not restricted to a single rotation. The duration of the frequency sweep of the reference signal 114 may be extended beyond the period of nominal rotation.

Figure 13:
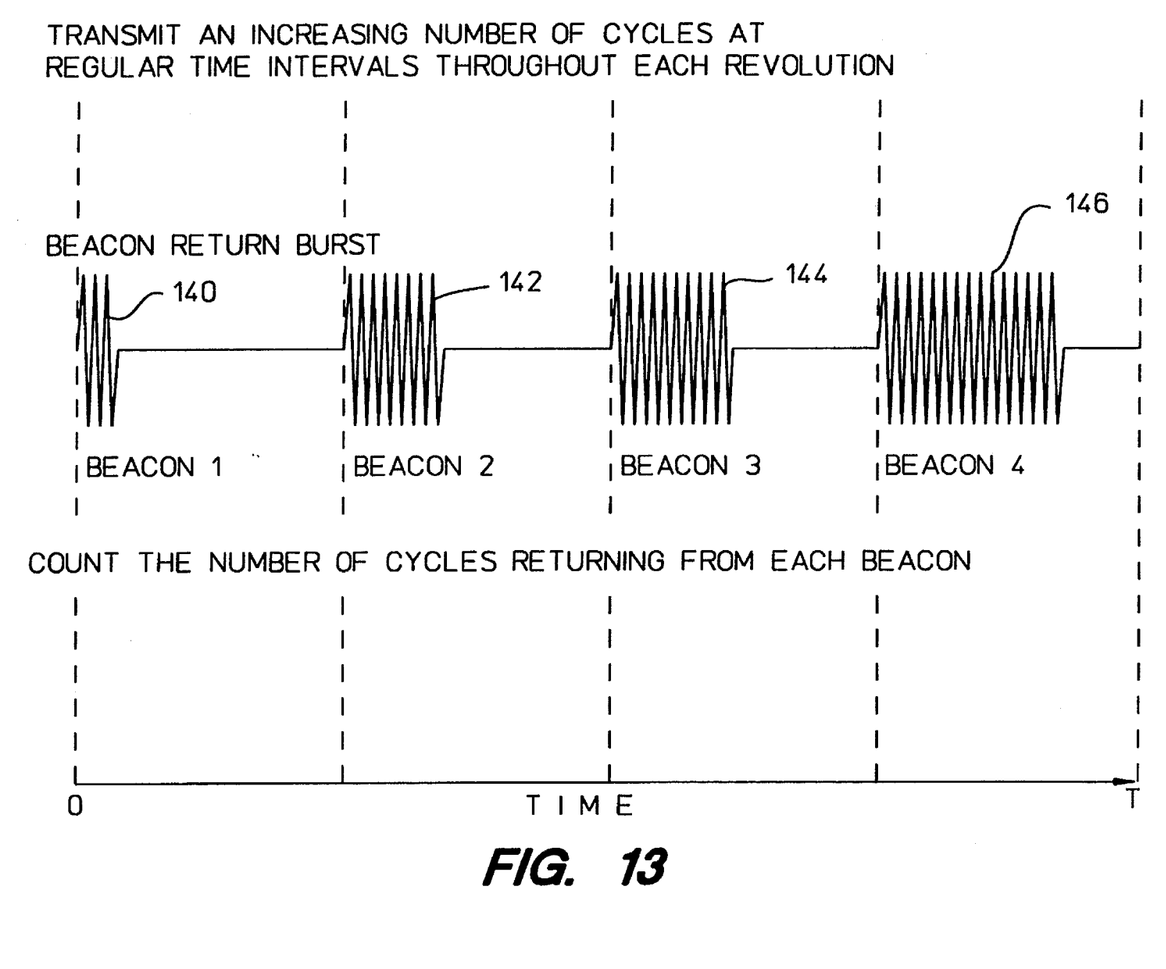
FIG. 13 is a sequence of ultrasound bursts having an increasing number of cycles in order to permit individual beacon identification in accordance with another embodiment of the invention.

Another method of individually identifying the four beacons 30, 32, 34 and 36 of FIG. 4 is described with reference to FIG. 13. In this embodiment, the method is based on broadcasting bursts 26 having a varying number of cycles. The number of cycles in a burst varies as a function of angular position. For example, a 3.5 French catheter has a transducer-to-sheath inner wall spacing of approximately 450 μm. The wavelength in water at 30 MHz is approximately 50 μm. Thus, a maximum of approximately 18 cycles can be transmitted, reflected at a beacon, and received by the imaging transducer. As an example, it will be presumed that there are 16 broadcasted bursts, with the first burst having three cycles and each successive burst increasing by an increment of one cycle, so that the last burst of the sequence has a total of 16 cycles. If the angular velocity of the catheter is uniform and correct, the imaging transducer will be in the anticipated angular position with each return burst. In FIG. 13, the first return burst 140 includes the three cycles of the first broadcasted burst. A seven-cycle return burst 142 will be directed from the second beacon 32, an eleven-cycle return burst 144 will be directed from the third beacon 34, and a fifteen-cycle return burst 146 will be directed from the fourth beacon 36. On the other hand, if the catheter is rotating too rapidly or too slowly, return bursts will have an insufficient number or an excessive number of cycles, respectively. The cycle count for each return burst can be monitored with a zero-crossing detector working in conjunction with a threshold detector. In order to implement this technique, it would be preferable to operate the imaging transducer at a frequency greater than 30 MHz, so that the number of cycles per angular increment can be increased. Angular velocity changes that occur over more than one revolution of the catheter can be corrected by monitoring the number of cycles returned from each beacon over more than one revolution period.

Figure 14:
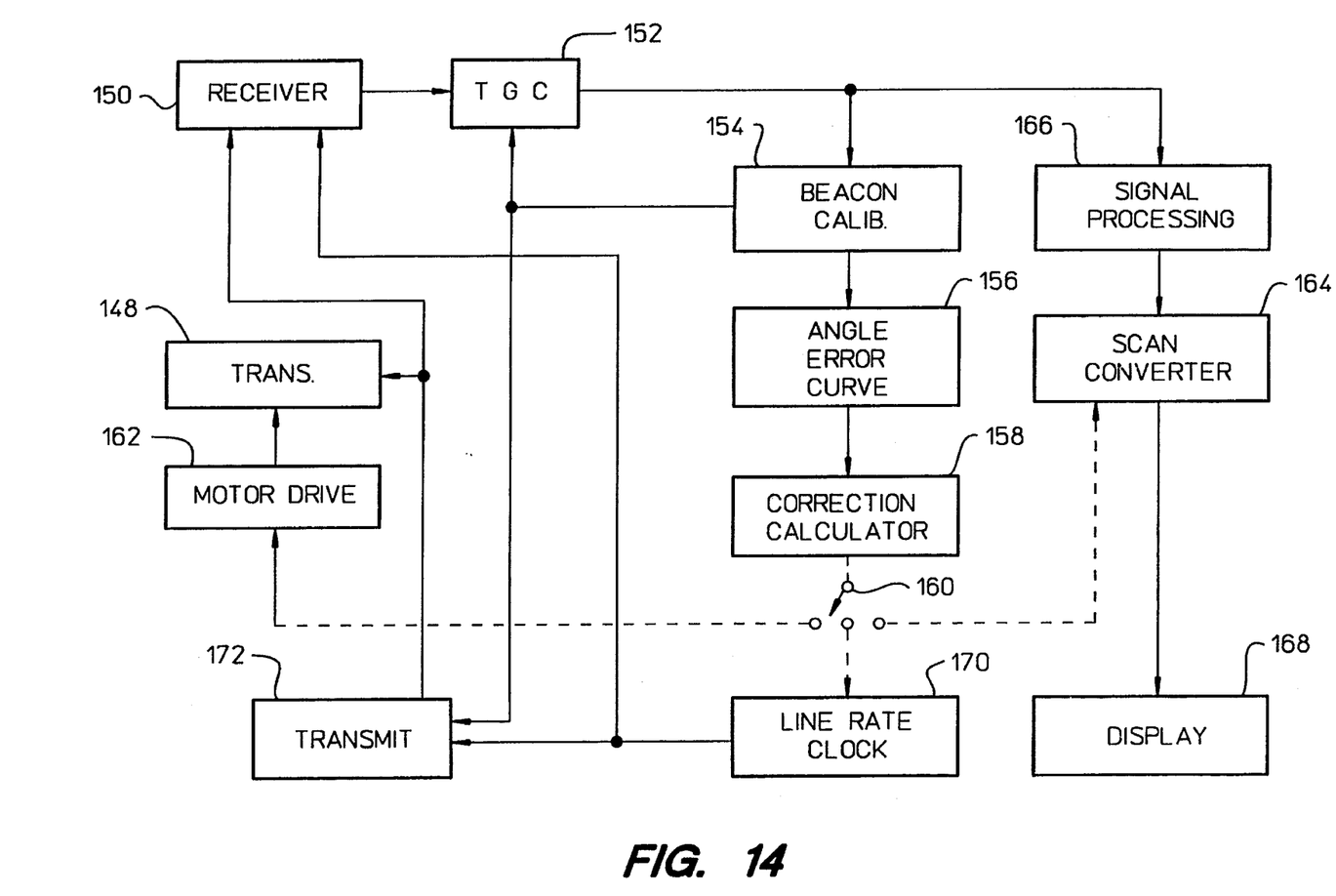
FIG. 14 is a block diagram of an ultrasound imaging system having adaptive compensation in accordance with the invention.

The cycle-count approach to correcting non-uniform angular velocity may be applied by the system of FIG. 14. Signals from the transducer 148 during an AEC calibration operation are passed to a receiver 150. A time gain control (TGC) 152 is set to attenuate signals beyond the desired beacon range. A beacon calibration module 154 passes the A-lines to an AEC module 156 that calculates the angular error curve and outputs the calculations to a line rate correction module 158. The line rate correction module is capable of providing compensation in any of the three approaches described above. Thus, depending upon the position of a switch 160, the module 158 will either (a) vary current to a drive motor 162 in order to reduce the velocity non-uniformities, (b) vary the scan converter algorithm 164 for mapping A-lines received at a signal processing module for accurate display 168 of the nonuniformly transmitted and received A-lines, or (c) vary the PRR as determined at a line rate clock 170, so that bursts are transmitted 172 at uniform spacing even though the angular velocity is nonuniform.

Other embodiments of the invention involving phase shifting have been contemplated. For example, passive or active beacons may be spaced apart from the imaging transducer by varying distances, so that the arrival time of return bursts may be used to identify individual beacons. This would effectively track one wall of the sheath. In an alternative embodiment, the wall thickness could be varied gradually going from a minimum to a maximum in one revolution. The variation in wall thickness could be measured using a higher frequency transducer mounted near the imaging transducer. Measured wall thickness would then uniquely identify individual lines.

In addition to acoustical encoding, optical, electrical and/or magnetic encoding may be employed. One advantage of the acoustical approach is that much of the required hardware is already in place in existing intravascular image systems. Nevertheless, other approaches are possible. Optical encoding may be performed by substituting light for the ultrasound and allowing the light to reflect off of reflectors located about the inner circumference of the catheter sheath. Electrical encoding may be performed by use of a commutator-type arrangement, wherein a signal is alternatingly switched on and off as a brush momentarily contacts conductive fingers placed on the inner circumference of the catheter sheath. Magnetic encoding may be performed by fixing a small magnetic member to the catheter so as to spin with the transducer. A single conductive loop with multiple "teeth," or a series of conductive loops, may be placed in the catheter wall about its circumference. The changing flux as the magnet is spun induces a voltage in the loop or loops, which can be picked up and used to determine angular velocity.

While the acoustical approach has been described and illustrated as being implemented with devices in which the transducer is located at the distal end of the probe, this is not critical. The techniques apply equally to embodiments in which ultrasonic energy is conducted to the distal end via an acoustic waveguide, as taught in U.S. Pat. No. 5,284,184 to Dias et al. The rotary pattern of ultrasound transmission can then be formed by rotating the end of the waveguide or by rotating a reflector.

We claim:

1. An ultrasound device for obtaining an image of an interior of a vessel comprising:

probe means for entering a body, said probe means having a proximal end and a distal end;

signal means for radiating a rotary pattern of ultrasonic energy from said distal end and for receiving reflected ultrasonic energy;

position-identification means for individually identifying a plurality of directions of radiation within said rotary pattern, said position-identification means including a plurality of beacons fixed within said rotary pattern to direct ultrasonic energy toward said signal means; and adaptive means, operatively associated with said position-identification means, for compensating for variations in angular velocity of said radiating said rotary pattern by said signal means, wherein said adaptive means reduces image distortions due to nonuniform angular velocity of said radiating.

2. The device of claim 1 wherein said signal means includes an ultrasonic transducer and a source of an excitation signal connected to said transducer, said source having means for varying characteristics of ultrasonic energy transmitted from said transducer in correspondence with an anticipated angular orientation of said transducer within said rotary pattern, said position-identification means being operative to interpret said varying characteristics of reflected ultrasonic energy from said beacons as being direction-indicative.

3. The device of claim 2 wherein said means for varying characteristics of said ultrasonic energy includes circuitry for varying a number of pulse cycles within a burst of ultrasonic energy in correspondence with said anticipated angular orientation of said transducer such that successive bursts differ with respect to said number of pulse cycles.

4. The device of claim 1 wherein said beacons are passive with respect to generating ultrasonic energy, said beacons being positioned within a field of view of said signal means so as to reflect ultrasonic energy to said signal means, said adaptive means being connected to distinguish each individual beacon of said plurality of beacons.

5. The device of claim 4 wherein each beacon of said plurality of beacons has an acoustic impedance that is different than acoustic impedances of all other beacons of said plurality of beacons, thereby enabling said adaptive means to distinguish each individual beacon of said plurality of beacons.

6. The device of claim 1 wherein said signal means includes a rotating transducer and wherein said position-identification means includes a source of a reference signal and includes processing circuitry for determining angular orientation of said transducer within said rotary pattern based upon a relationship between said reference signal and ultrasonic energy received by said transducer from said beacons.

7. The device of claim 6 wherein said source of said reference signal is a source of a signal having an increasing frequency during a selected time period.

8. The device of claim 7 wherein said processing circuitry includes means for mixing said reference signal and received electrical signals generated by said transducer in response to said ultrasonic energy from said beacons.

9. The device of claim 1 wherein said beacons are active ultrasonic transducers connected to an excitation signal source.

10. The device of claim 1 wherein said position-identification means includes structure for varying a phase of ultrasonic energy received from said beacons as a function of an angular orientation of said signal means within said rotary pattern.

11. The device of claim 1 wherein said adaptive means includes circuitry for varying timing of bursts of ultrasonic energy from said signal means based upon said nonuniform angular velocity.

12. The device of claim 1 further comprising a drive means for rotating said signal means, said adaptive means having a control circuit connected to said drive means for adjusting said drive means in real time in response to variations of angular velocity of said signal means.

13. The device of claim 1 wherein said signal means is a transducer and wherein said adaptive means includes an imaging system having means for determining a difference between an actual rotational speed and an anticipated rotational speed of said transducer, said imaging system further having means for time-adjusting electrical signals received from said transducer in response to receiving said reflected ultrasonic energy, said time-adjusting being selected to compensate for said difference between said actual and said anticipated rotational speed.

14. An ultrasound device for intravascular imaging comprising:

an elongated probe having a proximal end and a distal end, said distal end having an acoustic window for passage of ultrasonic energy;

an ultrasonic transducer connected to said probe to transmit and receive ultrasonic energy through said window;

a plurality of transducer beacons disposed within a field of view of said transducer through said window, said beacons being connected to generate ultrasound beacon signals, each of said beacons being positioned to direct said beacon signals toward said transducer;

drive means for rotating said transducer;

excitation source means for exciting said transducer such that periodic bursts of ultrasonic energy are emitted;

means, responsive to ultrasonic energy received from said beacons by said transducer, for identifying individual beacons of said plurality of beacons, thereby determining positions of said transducer during said periodic bursts of ultrasonic energy;

imaging means connected to said transducer for forming an image based upon reflected energy; and compensation means, responsive to said means for identifying, for adaptively adjusting at least one of said excitation source means, said drive means and said imaging means upon detection of a difference between an anticipated angular velocity and an actual angular velocity of said transducer.

15. The device of claim 14 wherein said beacons have electrode layers connected to apply a potential difference across a piezoelectric layer.

16. The device of claim 15 wherein said electrode layers are connected to a source-indicative means for supplying an electrical signal.

17. The device of claim 14 wherein said compensation means is connected to said excitation source to vary timing of said periodic bursts upon detection of said difference between anticipated and actual angular velocity.

18. The device of claim 14 wherein said compensation means includes control circuitry connected to said drive means to vary current to said drive means.

19. A method of operating an intravascular ultrasonic imaging device comprising the steps of:

inserting a distal end of said imaging device into a body of interest;

rotating an ultrasonic transducer located within said distal end;

periodically exciting said transducer such that periodic bursts of ultrasonic energy are transmitted from said distal end during each rotation of said transducer;

providing a plurality of beacons within a field of view of said transducer such that ultrasonic energy directed by said beacons is sensed by said transducer;

identifying ultrasonic energy directed to said transducer by each beacon as being from a particular beacon of said plurality of beacons;

forming an image of a portion of said body of interest surrounding said distal end in response to reflection of ultrasonic energy from said portion; and based upon said step of identifying, adaptively compensating for variations in angular velocity during rotation of said transducer such that image distortions due to said variations are reduced.

20. The method of claim 19 wherein said step of adaptively compensating is a step including adjusting timing of said step of periodically exciting said transducer.

21. The method of claim 19 wherein said step of providing beacons includes exciting said beacons to emit ultrasonic energy.

22. The method of claim 19 wherein said step of identifying said ultrasonic energy is a step of referencing a reference signal to signals generated by said transducer in response to reception of ultrasonic energy from said beacons.

* * * * *